(12) United States Patent
Varma et al.

(10) Patent No.: US 10,392,333 B2
(45) Date of Patent: Aug. 27, 2019

(54) METHOD OF PRODUCING FORMALDEHYDE FROM METHANOL

(71) Applicant: Purdue Research Foundation, West Lafayette, IN (US)

(72) Inventors: Arvind Varma, West Lafayette, IN (US); Yang Xiao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/226,500

(22) Filed: Dec. 19, 2018

(65) Prior Publication Data

US 2019/0194106 A1 Jun. 27, 2019

Related U.S. Application Data

(60) Provisional application No. 62/609,074, filed on Dec. 21, 2017.

(51) Int. Cl.
| | | |
|---|---|---|
| *C07C 45/29* | (2006.01) | |
| *B01J 23/00* | (2006.01) | |
| *B01J 23/644* | (2006.01) | |
| *B01J 21/18* | (2006.01) | |
| *B01J 21/08* | (2006.01) | |
| *C07C 47/04* | (2006.01) | |

(52) U.S. Cl.
CPC .......... *C07C 45/29* (2013.01); *B01J 23/6447* (2013.01); *B01J 21/08* (2013.01); *B01J 21/18* (2013.01); *C07C 47/04* (2013.01)

(58) Field of Classification Search
CPC ............................ C07C 45/29; B01J 23/6447
See application file for complete search history.

(56) References Cited

U.S. PATENT DOCUMENTS

| | | | | |
|---|---|---|---|---|
| 3,655,771 A | * | 4/1972 | Tadenuma | C07C 45/32 568/470 |
| 4,442,307 A | * | 4/1984 | Lewis | B01J 23/8876 568/470 |
| 6,781,018 B2 | * | 8/2004 | Liu | B01J 23/22 568/470 |
| 8,471,071 B2 | * | 6/2013 | Brenk | B01J 21/04 568/449 |

OTHER PUBLICATIONS

Yang et al. Low-temperature selective oxidation of methanol over Pt—Bi bimetallic catalysts. Journal of Catalysis, vol. 363, 144-153. (Year: 2018).*

* cited by examiner

*Primary Examiner* — Sikarl A Witherspoon
(74) *Attorney, Agent, or Firm* — Purdue Research Foundation

(57) ABSTRACT

A method for producing formaldehyde from methanol. The method includes the steps of packing a catalyst comprising platinum, bismuth and a support material into a reactor, introducing a reactant mixture containing methanol into the reactor such that the reactant mixture containing methanol is in close contact with the catalyst, and heating the reactant mixture containing methanol to a temperature for a period of time.

9 Claims, 5 Drawing Sheets

METHOD OF PRODUCING FORMALDEHYDE FROM METHANOL

CROSS-REFERENCE TO RELATED APPLICATIONS

The present U.S. patent application is related to and claims the priority benefit of U.S. Provisional Patent Application Ser. No. 62/609,074, filed Dec. 21, 2017, the contents of which are hereby incorporated by reference in their entirety into the present disclosure.

TECHNICAL FIELD

The present application relates to production of formaldehyde from methanol through selective oxidation of methanol, in the presence of catalysts, especially bimetallic catalysts.

BACKGROUND

This section introduces aspects that may help facilitate a better understanding of the disclosure. Accordingly, these statements are to be read in this light and are not to be understood as admissions about what is or is not prior art.

Selective partial oxidation of alcohols (e.g. methanol, ethanol, glycerol, etc.) over heterogeneous catalysts plays an important role in the production of bulk and fine chemicals, as well as in the conversion of biomass-derived compounds to renewable fuels and high value-added products. The correlation between catalyst properties and its performance (reactant conversion and selectivity towards a target product) benefits the development of efficient catalytic processes.

Methanol, the simplest alcohol, is used as a solvent, fuel for specialized vehicles or feedstock for the manufacture of other value-added chemicals, including formaldehyde and olefins. Methanol is considered as the simplest molecule probe candidate, owing to its representative structure, containing C—H, C—O and O—H bonds. About 40% of industrial methanol is converted to formaldehyde, and subsequently into diverse products such as plastics, plywood, paints and fibers. Remaining formaldehyde is consumed in the manufacture of textiles, paper, fertilizers and miscellaneous resinous products. Formaldehyde is produced commercially by catalytic selective oxidation of methanol. The most common processes of converting methanol to formaldehyde utilize supported silver (Ag) or molybdenum-iron (Mo—Fe) catalysts. The silver process operates at atmospheric pressure and the reaction temperature is in the range 560-600° C. Under these conditions, methanol conversion is typically 65-75%, while formaldehyde selectivity is about 90%. In the Mo—Fe process, an excess of air is used to ensure nearly 100% methanol conversion and avoid the explosive limits of methanol (6.7-36.5 vol. % in air). The reaction temperature is lower than that for the silver process, but yet in the range 250-400° C. The formaldehyde yield (methanol conversion times formaldehyde selectivity) is improved to 95%, with methanol conversion as high as 98-99%. Other catalyst candidates for methanol selective oxidation to formaldehyde have also been reported in the literature, including $VO_x$ (~400° C.), Cr—Mo (~300° C.), Fe—Cr—Mo (~300-360° C.), Mo—V—Cr—Bi—Si (~425° C.), $MoO_3$ (~300-350° C.) and $Bi_2O_3$—$MoO_3$ (280° C.). In all these cases, however, relatively high temperature (250-600° C.) is always used, leading to high energy and operating costs as well as large capital investment.

Using noble metals such as platinum (Pt) or pladium (Pd), low-temperature (<~120° C.) oxidation of methanol has been investigated previously. Owing to the superior activity over noble metals, however, formaldehyde production is limited using these catalysts because over-oxidized products (e.g. formic acid and $CO_2$) are typically generated. Using controlled Pd nano-particles with specific metal particle size as catalyst, the formaldehyde selectivity was only 20-30%. The use of Pt-based catalysts for formaldehyde production from methanol oxidation have also been reported. These, however, result in either low methanol conversion (<2.5%), or low selectivity towards target formaldehyde product. Recently, rather than over-oxidized products and formaldehyde, methyl formate was selectively (with selectivity>95%) synthesized by methanol coupling over Au catalysts. Similar high selectivity values towards methyl formate were also achieved over Pd-based catalysts.

In general, reducible oxides ($CeO_2$, $TiO_2$, $V_2O_5$, $Bi_2O_3$, etc.) can achieve high selectivity for certain non-over-oxidized products. Among these reducible oxide candidates, bismuth oxides show flexible oxidation states, including +1, +2, +3, +4 and +5, and typically +3. This suggests that Bi is a potentially good catalytic promoter for selective oxidation. When reducible oxides are used as promoters, in addition to noble metals, noble metal/reducible oxide interfaces are formed, which are able to tune selectivity towards target products by providing surface oxygen vacancy. In our prior works, some applications of bimetallic Pt—Bi catalysts were reported, e.g. glycerol conversion to 1,3-dihydroxyacetone (DHA), and guaiacol deoxygenation by the use of methane as reductant. Using density functional theory (DFT) in our recent publication, we concluded that the $BiO_x$ species is formed in situ at the interface of the originally reduced Pt—Bi bimetallic catalyst. A cooperative effect between Pt as the primary component and $BiO_x$ as the promoter was further identified for DHA formation from glycerol oxidation. Thus the Pt—$BiO_x$ interface favors O—H, rather than C—H, bond breaking. There is currently no available method which converts methanol to formaldehyde with high selectivity (e.g. >90%) at temperature<120° C.

Thus there is an unmet need for method which converts methanol to formaldehyde with high selectivity (e.g. >90%) at temperature<120° C.

SUMMARY

A method for producing formaldehyde from methanol is disclosed. The method includes the steps of packing a catalyst comprising platinum, bismuth and a support material into a reactor, introducing a reactant mixture containing methanol into the reactor such that the reactant mixture containing methanol is in close contact with the catalyst, and heating the reactant mixture containing methanol to a temperature for a period of time.

BRIEF DESCRIPTION OF DRAWINGS

Some of the figures shown herein may include dimensions. Further, some of the figures shown herein may have been created from scaled drawings or from photographs that are scalable. It is understood that such dimensions or the relative scaling within a figure are by way of example, and not to be construed as limiting.

Pt-0.2% Bi, 1% Pt-0.33% Bi and 1% Pt-2% Bi respectively, the rest being AC support. (Note: these are weight percentages)

Figure 1A:
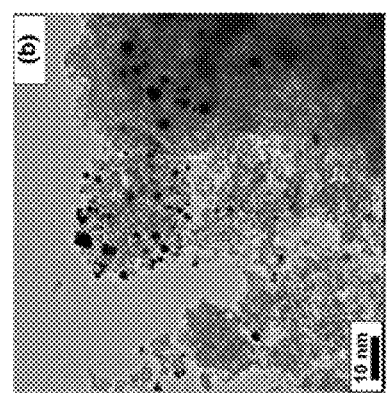
FIGS. 1A through 1D show Transmission Electron Microscopy (TEM) scans of Pt—Bi catalysts for 1% Pt, 1%
Figure 1B:
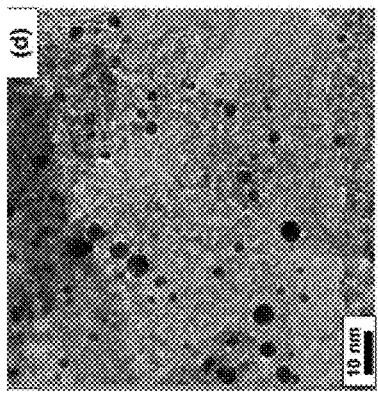
Figure 1C:
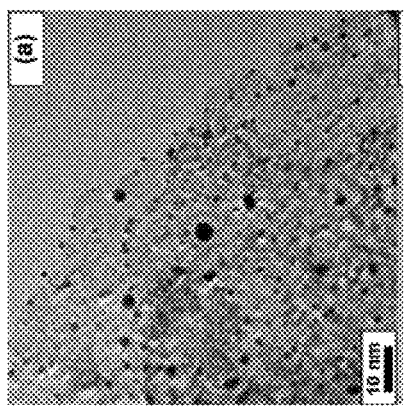
Figure 1D:
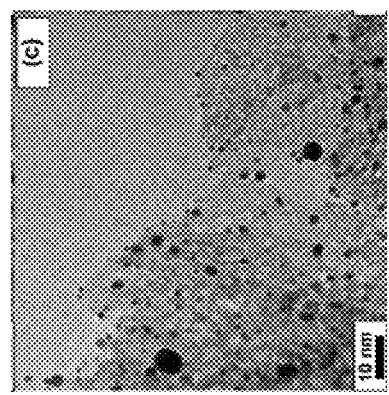
Figure 2:
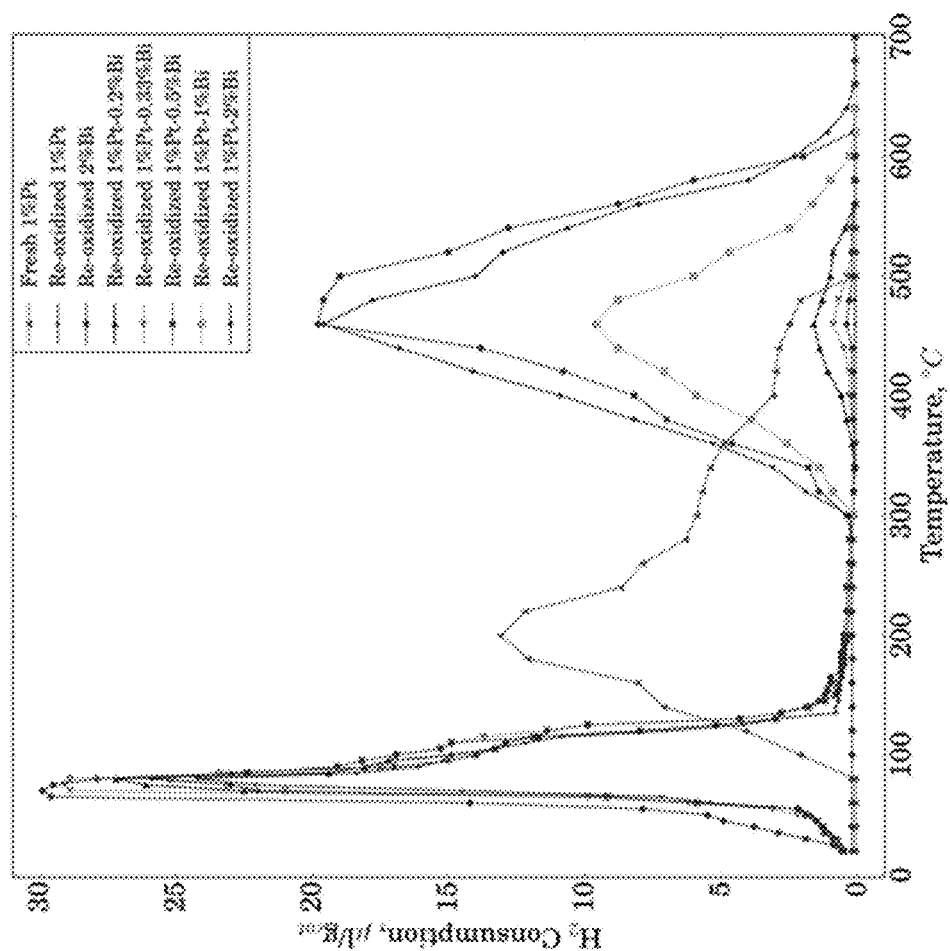

FIG. 2 shows $H_2$ Temperature-Programmed Reduction ($H_2$-TPR) of Various Materials.

Figure 3:
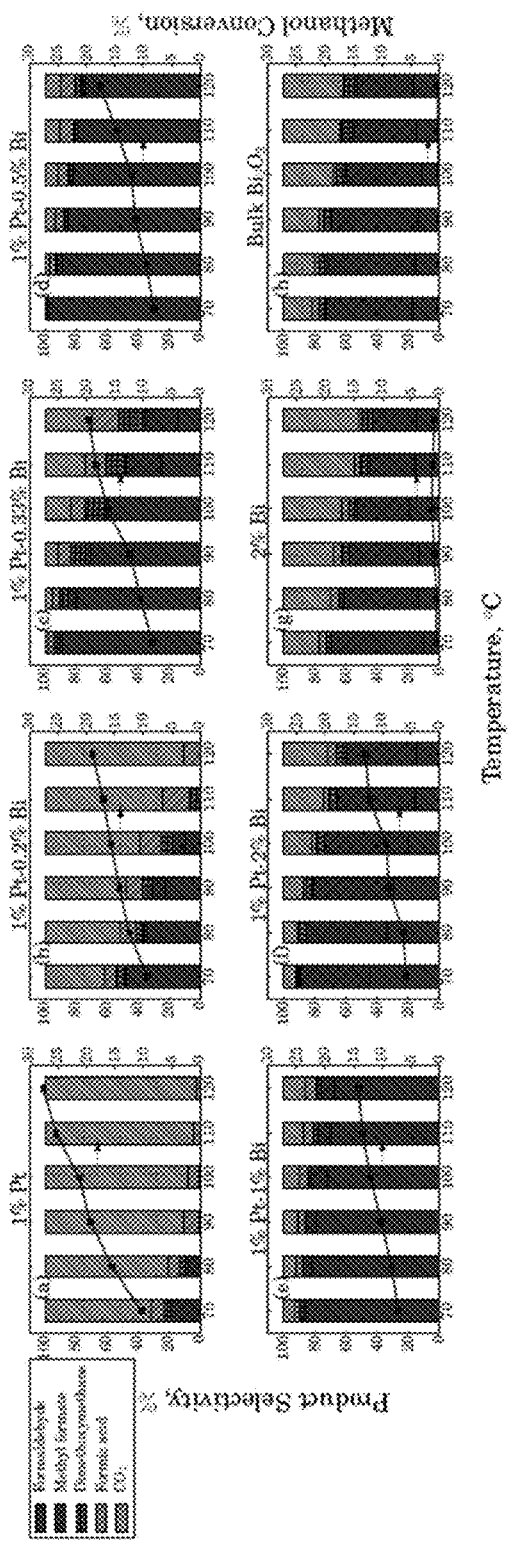

FIG. 3 shows Methanol Conversion and Selectivity toward Formaldehyde over Various Materials, referring to 1% Pt-y % Bi Catalysts, when y=0, 0.2, 0.33, 0.5, 1, and 2 as indicated; and, for 2% Bi and for bulk $Bi_2O_3$.

Figure 4:
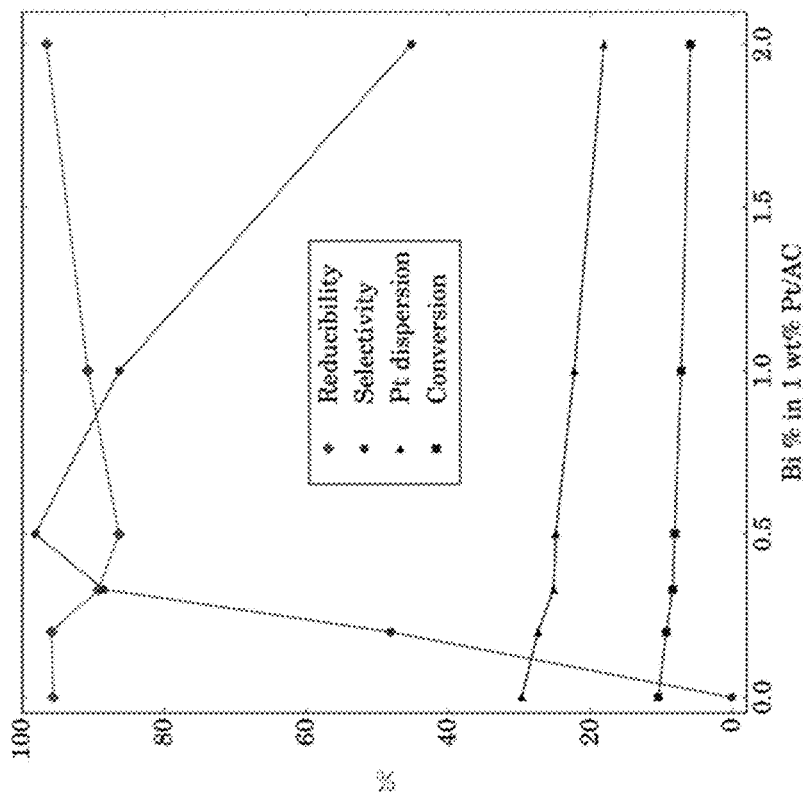

FIG. 4 shows Influence of Bi Content on Reducibility, Formaldehyde Selectivity, Pt Dispersion and Methanol Conversion. The y axis refers to percentage of these parameters influences by Bi content.

Figure 5B:
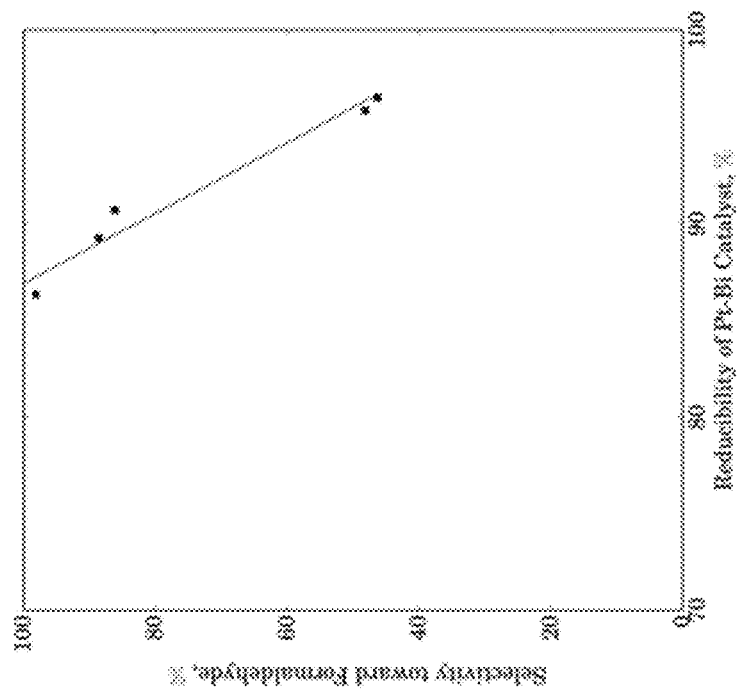
Figure 5A:
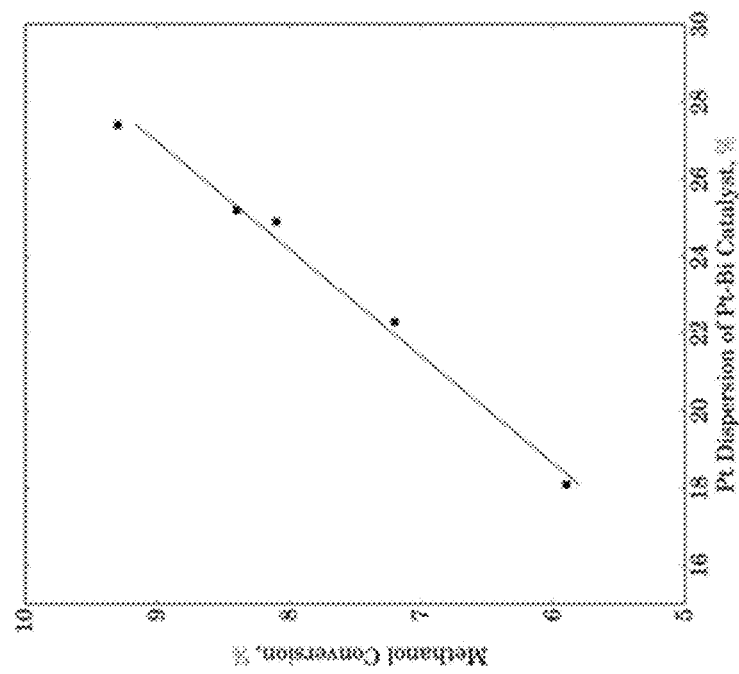

FIGS. 5A and 5B show Correlations of Pt Dispersion vs. Methanol Conversion and Reducibility vs. Formaldehyde Selectivity respectively.

DETAILED DESCRIPTION

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended.

In this description, it is disclosed that as a chemical probe molecule, methanol is converted to formaldehyde with high selectivity at relatively low temperatures. Based on performance tests in a fixed-bed reactor and catalyst characterization results, methanol conversion and selectivity toward formaldehyde are correlated with the properties of Pt—Bi-Support material catalysts. The catalytic mechanism and reaction pathway are proposed and discussed. The insight into selective oxidation of methanol over catalysts containing Pt—Bi bimetallic with support material provided in the present disclosure may lead to applications of similar bimetallic catalysts in selective oxidation of other alcohols.

In experiments leading to this disclosure, chloroplatinic acid hexahydrate (99.9% metal basis) and bismuth (III) chloride (99.999%), both from Sigma Aldrich, were used as precursors for Pt and Bi, respectively. The commercial bismuth (III) oxide was from Alfa Aesar. The activated carbon (AC) of 80-120 mesh, from Norit Americas Inc., was used as the catalyst support. The Pt—Bi catalysts were prepared by the following procedure as described in our prior works. Pt and Bi were loaded sequentially by the wet impregnation method. The Pt and Bi precursors were dissolved in diluted HCl solution and then added dropwise to the well-stirred AC slurry, with continued stirring for 8 hrs at room temperature (20° C.). The slurry was then rinsed two times and dried in air at 100° C. before use. Methanol (99%) and all other calibration compounds, including formaldehyde (37 wt % in water, with 7-8% methanol as stabilizer), methyl formate (97%), dimethoxymethane (98%) and formic acid (97%), were from Alfa Aesar. Ultra high purity grade gases (99.98% $O_2$, 99.999% Ar, 99.999% $N_2$, 99.98% He, 99.99% $CO_2$ and 99.999% $H_2$) were purchased from Indiana Oxygen. The 0.5% $Pt/Al_2O_3$ (metal dispersion=31±0.5%) standard, from Micromeritics, was used for $H_2$—$O_2$ titration calibration.

In the experiments leading to this disclosure, the Pt and Bi loadings were always on the AC support with a weight (wt) basis. For this reason, in later sections the weight basis and AC support are not noted explicitly when describing the catalysts. Thus, e.g., 1% Pt-1% Bi sample refers to 1 wt % Pt and 1 wt % Bi loaded on the AC support. Further, for purposes of this disclosure the term Pt—Bi catalyst or Pt—Bi bimetallic catalyst means a catalyst comprising Pt, Bi and AC support. Thus, in this disclosure, Pt—Bi catalyst and Pt—Bi bimetallic catalyst both refer to Pt+Bi+AC.

Various Pt—Bi-(AC support) catalysts used in the present work were characterized by BET (Brunauer-Emmett-Teller), $H_2$-TPR (Temperature-programmed reduction), ICP-AES (Inductively coupled plasma-atomic emission spectroscopy), TEM (transmission electron microscope), and powder XRD (X-ray Diffraction) techniques. By $N_2$ adsorption and desorption at 77 K via a Micromeritics ASAP 2000 apparatus, BET measurements were conducted, giving physisorption properties of catalysts, including surface area, pore size and pore volume. Before measurements, degassing was carried out at 300° C. for 8 hrs. Using 0.5% $Pt/Al_2O_3$ as calibration standard, Pt dispersion was obtained by the $H_2$—$O_2$ titration approach. Note that at room temperature, Bi does not adsorb $H_2$ molecules and bismuth oxide does not react with $H_2$. The TEM scans were operated at 200 kV with $LaB_6$ source (FEI-Tecnai). The TEM samples were prepared by suspending fine catalyst particles in ethanol, followed by dispersing them on 200 copper mesh grids with lacey carbon film coating, and then drying in air at room temperature. The powder XRD was carried out on an Rigaku SmartLab X-ray diffractometer with a CuKα radiation source. Elemental analysis of catalysts was carried out by the ICP-AES method (SPECTRO Instrument).

For $H_2$-TPR tests, 5 vol % $H_2$ and 5 vol % $O_2$ in $N_2$, prepared in situ by adjusting their flow rates via mass flow controllers, were used as oxidation and reduction gases, respectively. The standard $H_2$-TPR operations included the following steps:

(i) Drying the sample at 200° C. in 5 vol % $O_2$ for 1 hr;
(ii) Reducing the sample at 400° C. in 5 vol % $H_2$ for 2 hr;
(iii) Re-oxidizing the sample at 120° C. in 5 vol % $O_2$ for 1 hr;
(iv) TPR measurements by feeding 5 vol % $H_2$ in the range from room temperature to 700° C.

The heating rate was 5° C./min and the standard catalyst packed weight was 0.50 g. The total gas flow rate was 100 mL/min. The $H_2$ consumption was measured by a binary gas analyzer equipped with a thermal conductivity detector (TCD).

Catalytic performance tests were conducted in a fixed-bed reactor. Prior to reaction, the packed catalyst was activated at 400° C. for 4 hours under a gas mixture flow ($H_2$:$N_2$=1:2). The reactor was then purged by 50 mL/min $N_2$ for 15 min. The standard operating conditions were: 70° C., 1 atm, 0.02 g catalyst, methanol feed rate 0.6 mL/hr (liquid, at room temperature), preheated at 70° C. before entering the reactor, total gas flow rate 100 mL/min (corresponding to 6% $CH_3OH$, 1.5% $O_2$ and 92.5% $N_2$). The feed rates corresponded to a molar ratio of 4:1 between $CH_3OH$ and $O_2$, as 50% of the $O_2$ stoichiometric value described by Eq. 1 below. The use of less $O_2$ for standard operating conditions was to suppress the generation of over-oxidized products (formic acid, $CO_2$, etc.).

$$2CH_3OH + O_2 \rightarrow 2HCHO + 2H_2O, \tag{1}$$

Blank tests of AC support with no Pt or Bi loading were carried out under standard operating conditions, with methanol conversion always less than 0.5%. All experiments have carbon mass balances of 94±2%. Possible factors affecting mass balance include liquid hold-up in various locations in the system and coke deposit on the catalyst. A GC (Agilent GC6890) with flame ionization detector (FID), equipped with a °DB-1701 column (30 m×0.25 mm) was used for quantitative analysis of liquid products. The gaseous effluent was analyzed using a Micro GC (Agilent 3000A) equipped with two columns (Column A, MolSieve 5 A, 10 m×0.32 mm; Column B: Plot U, 8 m×0.32 mm) and two TCDs. All experiments were repeated at least twice and good repeatability generally within less than 2% deviation was achieved for all quantitative analysis.

Table 1 below shows BET Characterization Results of Various Catalytic Materials.

TABLE 1

BET Characterization Results of Various Catalytic Materials

| Catalyst | BET Surface Area, $m^2/g$ | Pore Size, nm | Pore Volume, $cm^3/g$ |
|---|---|---|---|
| 1% Pt | 583 | 3.4 | 1.2 |
| 1% Pt-0.2% Bi | 539 | 3.8 | 1.5 |
| 1% Pt-0.33% Bi | 567 | 3.2 | 1.1 |
| 1% Pt-0.5% Bi | 521 | 3.4 | 1.1 |
| 1% Pt-1% Bi | 508 | 2.9 | 0.9 |
| 1% Pt-2% Bi | 535 | 3.0 | 1.0 |
| 2% Bi | 511 | 2.6 | 0.7 |
| Bulk $Bi_2O_3$ | 6 | 12.2 | 0.22 |

As shown in Table 1, all catalysts supported on AC exhibited similar high surface areas (500-600 $m^2/g$), pore size (2.9-3.8 nm) and pore volume (0.7-1.5 $cm^3/g$). For bulk $Bi_2O_3$, all these values were very different. The data for both AC-based materials and $Bi_2O_3$ was consistent with prior works and literature report. The elemental analysis results of various Pt—Bi catalysts are listed in Table 2 below:

TABLE 2

AES-ICP Element Analysis of Various Catalytic Materials

| Catalyst | Pt % (fresh) | Bi % (fresh) | Pt % (used) | Bi % (used) |
|---|---|---|---|---|
| 1% Pt | 0.97 | — | 0.93 | — |
| 1% Pt-0.2% Bi | 0.94 | 0.21 | 0.92 | 0.19 |
| 1% Pt-0.33% Bi | 0.97 | 0.35 | 0.94 | 0.33 |
| 1% Pt-0.5% Bi | 0.95 | 0.48 | 0.93 | 0.46 |
| 1% Pt-1% Bi | 0.94 | 1.08 | 0.92 | 1.06 |
| 1% Pt-2% Bi | 0.98 | 2.06 | 0.95 | 2.03 |
| 1% Bi | — | 2.03 | — | 1.98 |

For fresh catalysts, both Pt and Bi compositions were close to the designed metal values, while for used catalysts, 2-4 wt % loss was found for both metals. This unavoidable metal leaching was typically reported in the literature. The XRD patterns of various bimetallic Pt—Bi catalysts showed no significant peaks in the range of 5-90°, likely owing to the high metal dispersion values and the amorphous structure of AC. The TEM scans of four representative Pt—Bi bimetallic catalysts are shown in FIG. 1. The scans indicate that metals (dark dots) were successfully loaded on AC supports. Table 3 below shows that Pt dispersion values are in the range 18.1-29.7%, while metal particle size values calculated by TEM scans and $H_2$—$O_2$ titration are essentially consistent.

TABLE 3

TEM and $H_2$—$O_2$ Titration Results of Various Catalytic Materials

| Catalyst | Particle Size, nm | | Pt Dispersion, % |
|---|---|---|---|
| | TEM | $H_2$—$O_2$ Titration | |
| 1% Pt | 2.7 | 3.9 | 29.7 |
| 1% Pt-0.2% Bi | 3.7 | 3.3 | 27.4 |

TABLE 3-continued

TEM and $H_2$—$O_2$ Titration Results of Various Catalytic Materials

| Catalyst | Particle Size, nm | | Pt Dispersion, % |
|---|---|---|---|
| | TEM | $H_2$—$O_2$ Titration | |
| 1% Pt-0.33% Bi | 3.5 | 3.6 | 25.2 |
| 1% Pt-0.5% Bi | 3.2 | 3.6 | 24.9 |
| 1% Pt-1% Bi | 3.8 | 3.7 | 22.3 |
| 1% Pt-2% Bi | 4.3 | 4.0 | 18.1 |
| 2% Bi | 3.9 | — | — |

The $H_2$-TPR profiles of various catalytic materials used in the present work are shown in FIG. 2. Based on quantitative Pt and Bi reduction, the $H_2$ consumption was calculated by integrating the curves in FIG. 2 and is listed in Table 4 below.

TABLE 4

$H_2$ Temperature-Programmed Reduction ($H_2$-TPR) Results of Various Treated Catalytic Materials

| Catalyst | $H_2$ Consumption, $\mu L/g_{cat}$ | | | Reducibility, % |
|---|---|---|---|---|
| | Experiment | Theory for $Pt^{2+}$-$Bi^{3+}$ | Theory for $Pt^{2+}$-$Bi^{+}$ | |
| 1% Pt | 1098 | 1149 | 1149 | 95.56 |
| 1% Pt-0.2% Bi | 1410 | 1471 | 1256 | 95.58 |
| 1% Pt-0.33% Bi | 1499 | 1680 | 1326 | 89.23 |
| 1% Pt-0.5% Bi | 1687 | 1954 | 1471 | 86.34 |
| 1% Pt-1% Bi | 2502 | 2758 | 1685 | 90.72 |
| 1% Pt-2% Bi | 4215 | 4367 | 2111 | 96.52 |
| 2% Bi | 3084 | 3218 | 1072 | 95.83 |

Referring to FIG. 2, the untreated 1% Pt started to reduce at ~100° C., lasting until 500° C., and a reduction peak appeared at about 200° C. In contrast, the re-oxidized (after reduction) 1% Pt was reduced between room temperature to 150° C., with a reduction peak at ca. 100° C. The total $H_2$ consumption of the re-oxidized [i.e. after step (iii) of the TPR procedure] 1% Pt was 1098 $\mu L/g_{cat}$ (see Table 4), which was close to the theoretical $H_2$ consumption for Pt reduction (1149 $\mu L/g_{cat}$). The untreated 1% Pt TPR curve, however, resulted in a larger $H_2$ consumption, likely owing to higher oxidized status of Pt (e.g. Pt), chloride salt formed during catalyst preparation or adsorbed organic species over the catalyst surface. The shift of reduction peak location to lower temperature suggests the ease of reducibility for re-oxidized 1% Pt catalyst, as compared to the untreated one. This also clarifies the need for catalyst activation by $H_2$ treatment prior to performance tests, as described earlier.

In FIG. 2, 2% Bi catalyst showed no reduction peak before 300° C., while reduction occurred between ca. 300-600° C. The reduction peak was at 450-500° C., consistent with $Bi_2O_3$ reduction as reported in the literature. In Table 4, the $H_2$ consumption data for 2% Bi was 3084 $\mu L$/gcat, close to Bi reduction (3218 $\mu L$/gcat). For re-oxidized 1% Pt-0.2% Bi, 1% Pt-0.33% Bi and 1% Pt-0.5% Bi, two reduction peaks were observed, with the first at about 80-100° C., and the second at about 450-500° C., corresponding to Pt and Bi respectively. Interestingly, with increase of Bi content (maintaining the same 1% Pt content), the Bi reduction peak areas decreased in these three catalysts, while Pt reduction peak areas increased slightly. As reported in our prior work, Bi was proposed for the active site at Pt—Bi interface for selective oxidation of glycerol, indicating the interaction between the two metals. Hence theoretical $H_2$ consumption values for Pt and Bi reduction were also calculated in Table 4. It appears for all catalysts, the experimental $H_2$ consumptions was larger than prediction of Pt and Bi reduction. For 1% Pt-0.33% Bi and 1% Pt-0.5% Bi, however, the values were closer to Pt and Bi than to Pt and Bi. The total experimental $H_2$ consumptions for these two catalysts were smaller than theoretical values for Pt—Bi reduction. These features indicate strong interaction between Pt and Bi in the presence of oxygen. For the other two catalysts (1% Pt-1% Bi and 1% Pt-2% Bi), Bi reduction showed large peaks, while Pt reduction exhibited essentially the same magnitude peaks as compared to the 1% Pt case. The total $H_2$ consumptions of these two relatively high Bi content catalysts were close to theoretical values for Pt—Bi reduction, suggesting that in these cases, Pt and Bi likely did not interact closely.

To further elaborate $H_2$ consumptions of various Pt—Bi catalysts quantitatively, a term of reducibility is defined by Eq. 2.

$$\text{Reducibility} = \frac{\text{Experimental } H_2 \text{ consumption}}{\text{Theoretical } H_2 \text{ consumption for } Pt^{2+} \text{ and } Bi^{3+}} \quad (2)$$

Reducibility values, suggesting interaction between Pt and Bi metals, are shown in Table 4. As further described in later sections, reducibility is correlated with formaldehyde selectivity from methanol conversion.

The representative product compositions for low temperature oxidation of methanol under standard operating conditions are shown in Table 5 below.

TABLE 5

Representative Product Compositions of Methanol Low-Temperature Oxidation under Standard Operating Conditions.

|  | 1% Pt | 1% Pt-0.5% Bi | 2% Bi |
|---|---|---|---|
| Methanol | 89.6 | 91.9 | 99.4 |
| Formaldehyde | 0.01 | 7.95 | 0.06 |
| Methyl formate | 2.44 | 0.03 | 0.21 |
| Dimethoxymethane | 1.08 | 0.01 | 0.12 |
| Formic acid | 2.39 | 0.06 | 0.16 |
| $CO_2$ | 4.48 | 0.05 | 0.05 |

Referring to Table 5, over all three catalysts, formaldehyde, methyl formate, dimethoxymethane, formic acid and $CO_2$ were detected as products. As demonstrated in Introduction, formaldehyde is our target product in the present work. Over 1% Pt, the selectivity toward formaldehyde was low, although methanol conversion (10.4%) was slightly higher than for 1% Pt-0.5% Bi catalyst (8.1%). In contrast, over 2.0% Bi catalyst, methanol conversion was low (0.6%). Preferably, 1% Pt-0.5% Bi gave a high formaldehyde selectivity (98.1%) with methanol conversion 8.1%. Thus Table 5 describes that in the presence of Pt, Bi selectively promotes formaldehyde formation. Similar reactions, converting alcohols to aldehydes using molecular oxygen by selective cleavages of C—H and O—H bonds at the same carbon atom, were reported in our prior works and literature.

Methanol conversion and selectivity toward formaldehyde over various materials are shown in FIG. 3, where 1% Pt, 1% Pt-0.5% Bi, and 2% Bi sections correspond to the three catalysts used in Table 5. All eight catalysts from FIG. 3 demonstrate clearly that with temperature increase, methanol conversion increases, while selectivity toward formaldehyde decreases. In FIG. 3, 1% Pt section shows that without Bi addition, formaldehyde selectivity is close to zero in the range of 70-120° C., although methanol conversion reaches about 30% at 120° C. With addition of only 0.2% Bi to 1% Pt (FIG. 3, Section 1% Pt-0.2% Bi), formaldehyde at 70° C. exhibits ca. 50% selectivity, although it drops to less than 5% at 120° C. FIG. 3, section labeled 1% Pt-0.33% Bi, with higher selectivity toward formaldehyde (90%-15%), gave similar trend as compared to FIG. 3, Section 1% Pt-0.2% Bi. From FIG. 3, for Bi contents 0.5% and 1%, respectively, selectivity toward formaldehyde shows relatively high and stable trends with temperature increase. For Bi content of 2% (from FIG. 3), however, selectivities toward formaldehyde at both 70 and 120° C. are less as compared with Bi contents of 0.5% and 1%. In the absence of Pt, illustrated by FIG. 3 (for 2% Bi and bulk $Bi_2O_3$), methanol conversions are less than 2%, indicating that Pt is necessary to activate methanol and/or $O_2$. Overall, FIG. 3 shows that at 70° C. (close to methanol boiling point 65° C.), specific Pt—Bi bimetallic catalysts provide high formaldehyde selectivity with methanol conversion 8%.

In FIG. 4, at 70° C., the influence of Bi contents in Pt—Bi catalysts on methanol conversion, formaldehyde selectivity, Pt dispersion and reducibility are plotted as a percentage. It shows that with Bi content increase, both Pt dispersion (also see Table 3) and methanol conversion decrease slightly. This leads to essentially the same TOF (turnover frequency, methanol molecules reacted per active Pt site per second). The Pt dispersion decrease was likely because more Bi segregation occurred over Pt surface when more Bi was added to Pt catalysts. The selectivity toward formaldehyde exhibits dramatic change with variation of Bi content, reaching the highest value (98.1%) at Bi content 0.5%. The reducibility, as measured by $H_2$-TPR and defined in Eq. 2 shows an opposite trend of the selectivity curve. These properties can thus be correlated with catalytic performance, as discussed below.

The correlations of Pt dispersion vs. methanol conversion and reducibility vs. formaldehyde selectivity are plotted in FIG. 5. It shows that Pt dispersion and methanol conversion correlate well by a linear fit. It appears that for the temperature range investigated (70-120° C.), the TOF values for methanol conversion over the various Pt—Bi catalysts were essentially constant (about 1.3 $s^{-1}$). The relationship of Pt—Bi reducibility and formaldehyde selectivity shows a good linear fit as well, demonstrating that for easier Pt—Bi catalyst reduction (i.e. less $H_2$ required to fully reduce catalyst), the formaldehyde selectivity is higher Similar trends for reducibility have also been reported previously for other reactions. As shown in Table 4 and FIG. 2, it appears that in the presence of molecular oxygen, both Pt and Bi are oxidized. With preferable ratios of Pt:Bi (1:1 to 5:1) in the present disclosure, the two metals interact strongly, likely creating Pt and partially lower oxidized state than Bi as the active site for selective oxidation of methanol. This specific catalyst type favors cleavage of O—H and C—H bonds from the same carbon atom.

Thus, in experiments leading to this disclosure, various Pt—Bi bimetallic catalysts were designed, prepared, characterized by BET, ICP-AES, $H_2$-TPR, TEM, and XRD, and tested in a fixed-bed reactor for low-temperature (70-120° C.) methanol selective oxidation, generating formaldehyde as the target product. The highest selectivity toward formaldehyde was 98% over the 1% Pt-0.5% Bi catalyst at 70° C., with methanol conversion 8.1%. The catalytic performance correlated well with properties of the Pt—Bi bimetallic catalysts. In particular, the reducibility of Pt—Bi catalysts exhibits a linear relationship with formaldehyde selectivity, while methanol TOF values are essentially constant. As compared to commercial formaldehyde manufacture techniques, this disclosure provides a new catalyst under relatively low temperatures, leading to potentially lower operating costs and capital investment. This work can also provide opportunities for selective oxidation of other alcohols (e.g. ethanol) under low temperatures.

From the foregoing detailed description, it is an objective of this disclosure to describe a method for producing formaldehyde from methanol. The method includes packing or placing a catalyst comprising Pt (primary metal), Bi (promoter) and a support material into a reactor, and introducing a reactant mixture containing methanol into the reactor in which the catalyst is placed such that the reactant mixture containing methanol comes into contact with the catalyst. Such packing or placing the catalyst in the rector is generally well understood by those skilled in the art. The reactant mixture containing methanol is then heated to a temperature for a period of time.

It should be noted that some embodiments of the methods of this disclosure, the reactor is a tubular reactor.

A non-limiting range of the temperature to which is the reactant mixture is heated in the reactor is in the non-limiting range of 273 K-423 K. In some versions of the method, the reactant mixture can include an inert gas such as, but not limited to argon or helium or nitrogen or a combination thereof.

Methods of using support materials them are well known to those skilled in the art and are well described in literature. A non-limiting range for particles comprising such a support material is 200 mesh to 10 mesh. Examples of such support materials suitable for the methods of this disclosure include but not limited to activated carbon and silicon dioxide ($SiO_2$). If activated carbon is used a support material, a non-limiting range for the specific surface area of the activated carbon is 200-2000 $m^2/g$.

The platinum loading in the "platinum-bismuth-support material" combination is in the non-limiting range of 0.1 to 5.0 weight percent. The bismuth loading in the "platinum-bismuth-support material" combination is in the non-limiting range of 0.1 to 5.0 weight percent. An example of such loading is 2% Pt-3% Bi-95% AC.

While the present disclosure has been described with reference to certain embodiments, it will be apparent to those of ordinary skill in the art that other embodiments and implementations are possible that are within the scope of the present disclosure without departing from the spirit and scope of the present disclosure. Thus, the implementations should not be limited to the particular limitations described. Other implementations may be possible. It is therefore intended that the foregoing detailed description be regarded as illustrative rather than limiting. Thus, this disclosure is limited only by the following claims.

The invention claimed is:

1. A method for producing formaldehyde from methanol, the method comprising:
   packing a catalyst comprising platinum, bismuth and a support material into a reactor;
   introducing a reactant mixture containing methanol into the reactor such that the reactant mixture containing methanol is in close contact with the catalyst; and
   heating the reactant mixture containing methanol to a temperature for a period of time.

2. The method of claim 1, wherein the operating temperature is in the range 273 K-423 K.

3. The method of claim 1, wherein the reactant mixture includes an inert gas.

4. The method of claim 3, wherein the inert gas is one of argon, helium and nitrogen.

5. The method of claim 1, wherein platinum loading in the catalyst is in the range of 0.1-5.0 weight %.

6. The method of claim 1, wherein bismuth loading in the catalyst is in the range of 0.1-5.0 weight %.

7. The method of claim 1, wherein the support material is one of activated carbon and $SiO_2$.

8. The method of claim 1, wherein the particle size of the support material is from 200 mesh to 10 mesh.

9. The method of claim 1, the reactor is a tubular reactor.

* * * * *